US010921466B2

(12) United States Patent
Miura et al.

(10) Patent No.: US 10,921,466 B2
(45) Date of Patent: Feb. 16, 2021

(54) RADIATION IMAGING APPARATUS AND RADIATION IMAGING SYSTEM

(71) Applicant: CANON KABUSHIKI KAISHA, Tokyo (JP)

(72) Inventors: Ryosuke Miura, Ichikawa (JP); Minoru Watanabe, Yokohama (JP); Keigo Yokoyama, Kawasaki (JP); Masato Ofuji, Takasaki (JP); Kentaro Fujiyoshi, Tokyo (JP); Jun Kawanabe, Saitama (JP); Sho Sato, Tokyo (JP); Kazuya Furumoto, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 63 days.

(21) Appl. No.: 16/456,854

(22) Filed: Jun. 28, 2019

(65) Prior Publication Data
US 2019/0324156 A1    Oct. 24, 2019

Related U.S. Application Data

(63) Continuation of application No. PCT/JP2017/047230, filed on Dec. 28, 2017.

(30) Foreign Application Priority Data

Jan. 18, 2017   (JP) .............................. JP2017-006978

(51) Int. Cl.
*G01T 1/20*    (2006.01)
*A61B 6/00*    (2006.01)
(Continued)

(52) U.S. Cl.
CPC .............. *G01T 1/20* (2013.01); *A61B 6/4233* (2013.01); *A61B 6/5258* (2013.01); *G01T 7/00* (2013.01); *H04N 5/32* (2013.01); *G01N 23/04* (2013.01)

(58) Field of Classification Search
CPC ........... G01T 1/20; G01T 7/00; A61B 6/4233; A61B 6/5258; A61B 6/563; A61B 6/542; A61B 6/585; H04N 5/32; G01N 23/04
See application file for complete search history.

(56) References Cited

U.S. PATENT DOCUMENTS 5,153,423 A * 10/1992 Conrads ................... G01J 1/44
                                                        250/208.1
6,393,098 B1 * 5/2002 Albagli .................... H04N 5/32
                                                        348/E5.079
(Continued)

FOREIGN PATENT DOCUMENTS

JP    2014-71034 A    4/2014
JP    2016-39463 A    3/2016
(Continued)

*Primary Examiner* — Marcus H Taningco
(74) *Attorney, Agent, or Firm* — Canon U.S.A., Inc. IP Division

(57) ABSTRACT

A radiation imaging apparatus includes a first detection pixel including a first switch element, a second detection pixel including a second switch element and having sensitivity which is different from that of the first detection pixel, a first signal line, a second signal line, a reading circuit which performs a first operation of reading first and second signals which appear in the first and second signal lines in a state in which the first and second switch elements are in a non-conductive state while the radiation imaging apparatus is irradiated with a radial ray and a second operation of reading third and fourth signals which appear in the first and second signal lines when the first and second switch elements are brought into a conductive state, and an information processing circuit which performs a process of generating information based on the first to fourth signals.

15 Claims, 14 Drawing Sheets

(51) Int. Cl.
*G01T 7/00* (2006.01)
*H04N 5/32* (2006.01)
*G01N 23/04* (2018.01)

(56) References Cited

U.S. PATENT DOCUMENTS

| | | |
|---|---|---|
| 2011/0127441 A1 | 7/2011 | Tanabe |
| 2015/0192684 A1 | 7/2015 | Ito |
| 2016/0041276 A1 | 2/2016 | Kawanabe |
| 2017/0201704 A1* | 7/2017 | Furumoto .............. H04N 5/361 |
| 2018/0006080 A1* | 1/2018 | Fujiyoshi .......... H01L 27/14612 |
| 2018/0055464 A1 | 3/2018 | Watanabe |

FOREIGN PATENT DOCUMENTS

| | | |
|---|---|---|
| JP | 2016-220116 A | 12/2016 |
| WO | 2010/010620 A1 | 1/2010 |

\* cited by examiner

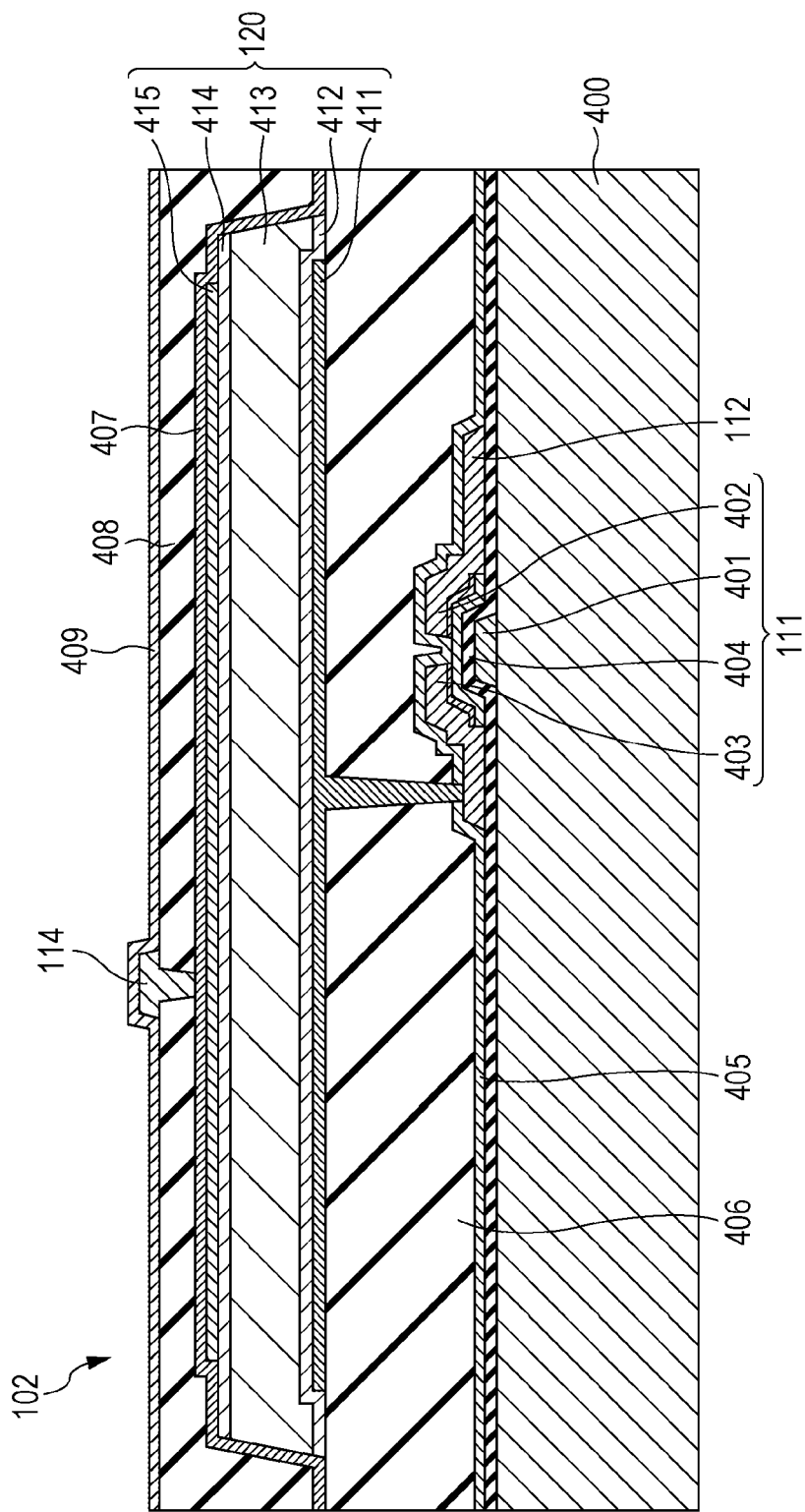

RADIATION IMAGING APPARATUS AND RADIATION IMAGING SYSTEM

CROSS-REFERENCE TO RELATED APPLICATIONS

This application is a Continuation of international Patent Application No. PCT/JP2017/047230, filed Dec. 28, 2017, which claims the benefit of Japanese Patent Application No. 2017-006978, filed Jan. 18, 2017, both of which are hereby incorporated by reference herein in their entirety.

TECHNICAL FIELD

The present invention relates to a radiation imaging apparatus and a radiation imaging system.

BACKGROUND ART

A radiation imaging apparatus including pixels arranged in a 2D array has been widely used. Each of the pixels include a conversion element which converts a radial ray into charge and a switch element, such as a thin-film transistor (TFT), in combination. In recent years, multiple functions of such a radiation imaging apparatus has been discussed, and a radiation imaging apparatus incorporating a function of automatic exposure control (AEC) as one of the multiple functions has been discussed. The AEC function is used by the radiation imaging apparatus to obtain irradiation information while a radiation source irradiates a radial ray.

PTL 1 discloses a radiation imaging apparatus including a plurality of pixels which are arranged in an array in an imaging region and which are used to obtain a radiation image. Furthermore, the radiation imaging apparatus disclosed in PTL 1 includes detection pixels which are arranged in the imaging region or adjacent to the imaging region and each of which includes a conversion element which converts a radial ray into an electric signal so as to obtain information on irradiation with a radial ray. Furthermore, the radiation imaging apparatus disclosed in PTL 1 includes a detection signal line which receives signals output from the detection pixels and a signal processing circuit which processes signals output from the detection pixels through the detection signal line. The detection pixels and the detection signal line are used to detect information on irradiation with a radial ray, such as a start of irradiation with a radial ray, an end of the irradiation, and an accumulated irradiation amount of a radial ray. Such a radiation imaging apparatus includes non-negligible parasitic capacitances between electrodes of the pixels for obtaining a radiation image and the detection signal line. Crosstalk may be generated through the parasitic capacitances due to variation of potentials of the electrodes of the pixels for obtaining a radiation image generated by irradiation with a radial ray. Signals supplied to the detection signal line include components of signals supplied from the pixels for obtaining a radiation image and components generated due to the crosstalk. It is difficult to reliably obtain a signal supplied from the radiation detection pixel during irradiation with a radial ray due to the crosstalk components. Therefore, the radiation imaging apparatus disclosed in PTL1 further includes a correction pixel having sensitivity to detection of a radial ray which is different from that of the detection pixel and a correction signal line which is disposed in the imaging region or adjacent to the imaging region and which receives a signal supplied from the correction pixel. In addition, in the radiation detection apparatus in PTL1, a signal processing circuit generates information on irradiation with a radial ray corrected such that influence of the crosstalk is reduced based on the signal supplied from the detection signal line and the signal supplied from the correction signal line.

CITATION LIST

Patent Literature

PTL 1 Japanese Patent Laid-Open No. 2016-220116

However, the information on irradiation with a radial ray obtained by the radiation imaging apparatus disclosed in PTL1 has a problem in correction accuracy. When parasitic capacitances of pixels associated with the detection signal line and parasitic capacitances of pixels associated with the correction signal line are different from each other, crosstalk which overlaps with the signals in the detection signal line and crosstalk which overlaps with the signals in the correction signal line are different from each other. This is because the number of pixels associated with the correction signal line may be different from the number of pixels associated with the detection signal line since the correction pixels are connected to the correction signal line. Reduction of influence of the difference leads to improvement of correction accuracy. Furthermore, distribution of intensity of an irradiated radial ray in a plane varies for each imaging, and crosstalk generated in the individual lines may vary depending on the number of detection pixels and the number of correction pixels having sensitivity different from that of the detection pixels in a region in which intensity of the Irradiated radial ray is high. Therefore, reduction of influence of the difference of the crosstalk generated for each imaging is required for improvement of correction accuracy.

The present invention provides a technique of correcting a change of a signal caused by crosstalk and improving reliability of detection of a radial ray by improving accuracy of the correction.

SUMMARY OF INVENTION

According to an embodiment of the present invention, a radiation imaging apparatus includes a plurality of pixels which are arranged in an array in an imaging region and which are for obtaining a radiation image, a first detection pixel including a first switch element and a second detection pixel including a second switch element and having sensitivity to detection of a radial ray which is different from sensitivity of the first detection pixel which are used to obtain information on irradiation with a radial ray on the imaging region including at least one of a start of irradiation with a radial ray, an end of irradiation with a radial ray, intensity of irradiation with a radial ray, and an amount of irradiation with a radial ray, a first signal line which is disposed in the imaging region or adjacent to the imaging region and which receives a signal supplied from the first detection pixel through the first switch element in a conductive state and a second signal line which receives a signal supplied from the second detection pixel through the second switch element in a conductive state, a reading circuit configured to perform a first operation of reading first and second signals which appear in the first and second signal lines in a state in which the first and second switch elements are in a non-conductive state while the radiation imaging apparatus is irradiated with a radial ray and a second operation of reading third and fourth signals which appear in the first and second signal lines when the first and second switch elements are brought into a conductive state, and an information processing circuit configured to perform a process of generating the information based on the first to fourth signals.

Further features of the present invention will become apparent from the following description of exemplary embodiments with reference to the attached drawings.

BRIEF DESCRIPTION OF DRAWINGS

FIG. 4 is a cross-sectional view of a pixel of the radiation imaging apparatus of FIG. 1.

DESCRIPTION OF EMBODIMENTS

Figure 1:
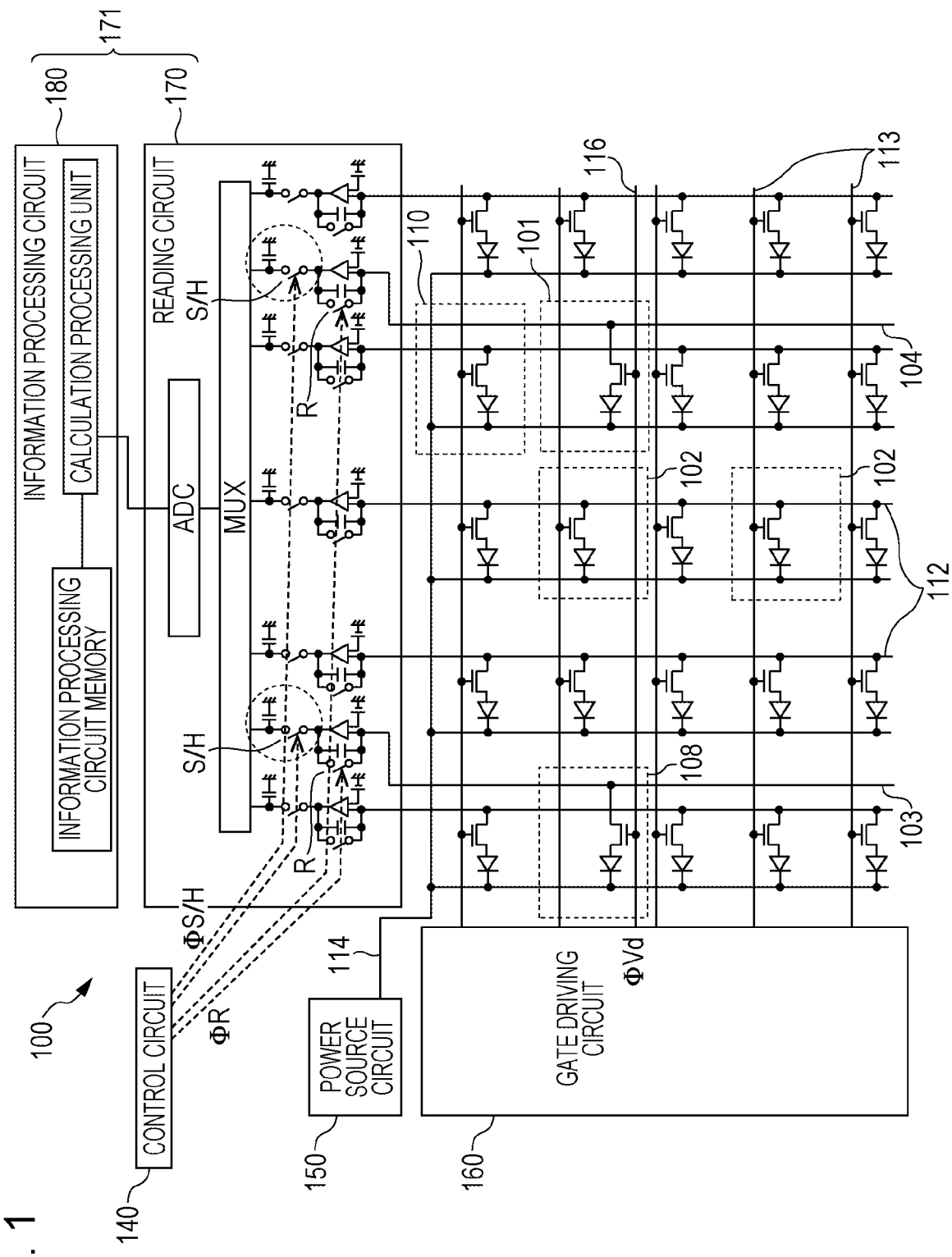
FIG. 1 is a diagram illustrating an equivalent circuit of a circuit configuration of a radiation imaging apparatus according to an embodiment of the present invention.

Hereinafter, an embodiment of a radiation imaging apparatus according to the present invention will be described in detail with reference to the accompanying drawings. Note that, in a description below and the drawings, common components in the plurality of drawings are denoted by common reference numerals. Therefore, common components are described by mutually referencing the plurality of drawings and descriptions of the components having the common reference numerals are omitted where appropriate. Note that examples of a radial ray in the present invention may include, in addition to an α ray, a β ray, and a γ ray which are beams formed of particles (including photons) emitted due to radioactive decay, beams having energy which is the same as that of the beams formed of particles or more, such as an X ray, a particle ray, and a cosmic ray.

A radiation imaging apparatus according to a first embodiment will be described with reference to FIGS. 1 to 9. FIG. 1 is a diagram illustrating an equivalent circuit indicating a circuit configuration of a radiation imaging apparatus 100 according to this embodiment. The radiation imaging apparatus 100 of this embodiment includes an imaging region including a plurality of pixels arranged in an array on a substrate and a peripheral region for controlling the pixels and processing electric signals output from the pixels.

Although the peripheral region includes a power source circuit 150 and a driving circuit 160 which drive and control the pixels, and a signal processing circuit 171 including a reading circuit 170 and an information processing circuit 180 which process electric signals output from the pixels, the present invention not limited to these. The reading circuit 170 and the information processing circuit 180 may be integrally configured, for example. The peripheral region of the radiation imaging apparatus 100 further includes a control circuit 140 which controls the signal processing circuit 171.

The imaging region includes a plurality of pixels used to obtain a radiation image and a plurality of detection pixels used to detect irradiation with a radial ray or to obtain irradiation information. In this embodiment, the term "pixels" include pixels 102 and pixels 110 having signal lines passing therethrough which transfer electric signals obtained by the detection pixels to the signal processing circuit 171. Furthermore, the term "detection pixels" includes a detection pixel 101 serving as a first detection pixel and a correction pixel 108 serving as a second detection pixel which output electric signals to the signal processing circuit 171 through different signal lines. The detection pixel 101 and the correction pixel 108 are used to obtain radial-ray irradiation information, separated from a radiation image, associated with irradiation with a radial ray, such as a start and an end of irradiation with a radial ray, irradiation intensity of a radial ray, and an amount of irradiation with a radial ray, at a time of irradiation with a radial ray. Since such a detection pixel 101 and such a correction pixel 108 are arranged, the radiation imaging apparatus 100 may incorporate an automatic exposure control (AEC) function. An equivalent circuit representing a portion of an imaging region in the radiation imaging apparatus 100 which includes pixels in a matrix of 5 rows by 5 columns is illustrated in FIG. 1.

The imaging region may include a single pixel area or a plurality of pixel areas including such a detection pixel 101 and such a correction pixel 108. In the radiation imaging apparatus 100, the pixel areas including the detection pixel 101 and the correction pixel 108 disposed therein are disposed in a matrix of 3 rows by 3 columns or rows by 5 columns, for example. By this, information on irradiation with a radial ray emitted to the individual pixel areas of the radiation imaging apparatus 100 may be detected for individual pixel areas. The imaging region including the plurality of pixel areas will be described hereinafter with reference to FIGS. 8 and 9.

Pixels 102 and 110 disposed in the imaging region of the radiation imaging apparatus 100 receive a power source from the power source circuit 150 through a power source line 114 and are controlled by the driving circuit 160 through image control lines 113. Electric signals output from the pixels 102 and 110 are transferred to the signal processing circuit 171 through image signal lines 112. In this way, a radiation image may be obtained. Furthermore, the detection pixel 101 and the correction pixel 108 receive the power source from the power source circuit 150 through the power source line 114 and are controlled by the driving circuit 160 through a detection control line 116. An electric signal output from the detection pixel 101 is transferred to the signal processing circuit 171 through a detection signal line 104 serving as a first signal line. An electric signal output from the correction pixel 108 is transferred to the signal processing circuit 171 through a correction signal line 103 serving as a second signal line. By obtaining the information on irradiation with a radial ray using the detection pixel 101 and the correction pixel 108, irradiation information including radiation amounts in regions where the detection pixel 101 and the correction pixel 108 are disposed may be obtained. In this embodiment, the detection signal line 104 and the correction signal line 103 are disposed in the imaging region. The detection signal line 104 and the correction signal line 103 may be disposed adjacent to an outer edge portion of the imaging region. Furthermore, the detection signal line 104 and the correction signal line 103 may be the same as some of the image signal lines 112. Furthermore, the detection control line 116 may be the same as one of the image control lines 113. Here, the reading circuit 170 includes reset switches R which are connected to the detection signal line 104 and the correction signal line 103, respectively, so as to reset the detection signal line 104 and the correction signal line 103. Furthermore, the reading circuit 170 includes a sample-and-hold circuit S/H which samples and holds an electric signal output from the detection pixel 101 through the detection signal line 104 so that the reading circuit 170 reads the electric signal. Furthermore, the reading circuit 170 includes a sample-and-hold circuit S/H which samples and holds an electric signal output from the correction pixel 108 through the correction signal line 103 so that the reading circuit 170 reads the electric signal. The control circuit 140 supplies a control signal ΦR used to control the reset switches R to the reset switches R. Furthermore, the control circuit 140 supplies a control signal ΦS/H used to control the sample-and-hold circuits S/H to the sample-and-hold circuits S/H.

In the radiation imaging apparatus 100, a radial ray is emitted to portions other than the detection pixel 101 and the correction pixel 108. When a radial ray is emitted, charge corresponding to an amount of emitted radial ray is generated and accumulated also in the pixels 102 and 110. Here, in the pixels 110 including the detection signal line 104 passing therethrough, the accumulated charge is transferred to the detection signal line 104 through the parasitic capacitances between the electrodes of the conversion elements of the pixels 110 which convert a radial ray into charge and the detection signal line 104 based on the principle of conservation of charge. As a result, a charge amount corresponding to an electric signal read from the detection signal line 104 includes charge supplied from the detection pixel 101 and charge transferred from the pixels 110 through the capacitances located between the detection signal line 104 and the conversion elements of the pixels 110. Accordingly, if an area of irradiation with a radial ray is increased and the number of pixels 110 irradiated with the radial ray is increased, an amount of charge transferred from the pixels 110 to the detection signal line 104 is increased. Furthermore, if an area which receives irradiation with a radial ray is reduced and the number of pixels 110 having charge accumulated therein due to the irradiation with the radial ray is reduced, an amount of charge transferred from the pixels 110 to the detection signal line 104 is reduced.

The correction signal line 103 is used to correct the transfer of the charge through the capacitances positioned between the detection signal line 104 and the pixels 110 through which the detection signal line 104 passes and cause the reading circuit 170 to appropriately read electric signals corresponding to an amount of a radial ray emitted to the detection pixel 101. For example, in a case where a shape of the correction signal line 103 is the same as a shape of the detection signal line 104 or the number of pixels 110 through which the correction signal line 103 passes is the same as the number of pixels 110 through which the detection signal line 104 passes, parasitic capacitances positioned between the pixels 110 and the correction signal line 103 and parasitic capacitances positioned between the pixels 110 and the detection signal line 104 are substantially the same. Consequently, an amount of charge transferred from the pixels 110 to the correction signal line 103 and an amount of charge transferred from the pixels 110 to the detection signal line 104 are substantially the same. An amount of charge which is a value of an electric signal supplied from the correction signal line 103 is subtracted from an amount of charge which is a value of an electric signal obtained by the detection signal line 104. By this subtraction (a difference process), an amount of charge equivalent to an amount of charge converted by the detection pixel 101 may be generated and obtained as information on a signal of the detection pixel 101. Various methods may be employed as a method for the subtraction. Analog subtraction or digital subtraction may be employed, for example. Furthermore, a correlated double sampling (CDS) circuit may be used, for example.

However, the signal processing circuit 171 and the like disposed near the imaging region heats when signal processing is performed, for example. Temperature and temperature distribution may not be uniform but may vary in the imaging region where the pixels 102 and 110 and the detection pixel 101 are disposed due to local heat. If the temperature varies, characteristics, such as a dark current, of the conversion elements disposed in the pixels 102 and 110 and the detection pixel 101 and characteristics, such as an offset level, of the thin-film transistors (TFTs) which are switch elements disposed in the pixels 102 and 110 and the detection pixel 101 may be changed. When a radial ray is to be detected, the detection pixel 101 is turned on and the TFTs of the pixels 102 and 110 are turned off. In this case, not only a component generated due to the irradiation with a radial ray but also change components of the characteristics, such as the offset level and the dark current, of the detection pixel 101 which is turned on are superposed on a difference of electric signals between the correction signal line 103 and the detection signal line 104. When the characteristics including the dark current and the offset level of the detection pixel 101 are changed, a value of an electric signal obtained by the difference is also changed. For example, in a case where an offset level of the detection pixel 101 is increased due to increase in temperature, an extracted electric signal may exceed a threshold value for detection of a radial ray even if irradiation with a radial ray is not performed. In this case, it is recognized that irradiation with a radial ray has been performed even if irradiation with a radial ray has not been performed.

To address this problem, the correction pixel 108 which has a structure of the conversion element and a structure of the TFT of the detection pixel 101 connected to the detection signal line 104 in this embodiment and which is connected to the correction signal line 103 is disposed in the imaging region of the radiation imaging apparatus 100. The correction pixel 108 may be turned on simultaneously with the detection pixel 101. In FIG. 1, the correction pixel 108 and the detection pixel 101 are controlled by the same detection control line 116 and simultaneously turned on by a driving signal ΦVd. Furthermore, the correction pixel 108 may be disposed in the vicinity of the detection pixel 101. A temperature and a temperature distribution near the detection pixel 101 in the imaging region are changed, and the characteristics of a dark current and an offset level are changed in the pixels 102 and 110 and the detection pixel 101. However, when the correction pixel 108 having a temperature characteristic equivalent to that of the detection pixel 101 is disposed in the vicinity of the detection pixel 101, the dark current, the offset level, and the like may be subtracted even in a case where the characteristics of the dark current, the offset level, and the like of the detection pixel 101 are changed. Consequently, information on irradiation with a radial ray on the detection pixel 101 may be accurately generated and obtained.

However, since the correction pixel 108 and the detection pixel 101 have the conversion elements and the TFTs of the same structures as described above, a difference between amounts of charge corresponding to electric signals output relative to amounts of radial rays incident on the correction pixel 108 and the detection pixel 101 is small. When a difference between outputs from the correction pixel 108 and the detection pixel 101 is small, it is difficult to obtain information on a signal of the detection pixel 101 only by obtaining a difference between charge amounts of the detection signal line 104 and the correction signal line 103. The detection pixel 101 and the correction pixel 108 having the same structure of the conversion elements and the same structure of the TFTs are required to output different electric signals relative to an incident radial ray so that information on irradiation with a radial ray is generated. To output different electric signals, the detection pixel 101 and the correction pixel 108 may have different sensitivities for conversion of an incident radial ray into an electric signal. In this embodiment, sizes of regions for detecting a radial ray in the detection pixel 101 and the correction pixel 108 are different from each other, that is, the region for detecting a radial ray in the detection pixel 101 is larger than that of the correction pixel 108. For example, in a case of a radiation imaging apparatus which directly converts a radial ray into an electric signal, a shield member using heavy metal, such as lead, for shielding a radial ray may be disposed on the conversion element of the correction pixel 108. Furthermore, in a case of an indirect-type radiation imaging apparatus which converts a radial ray into light and converts the light into an electric signal using a scintillator, a shield film formed of aluminum serving as a shield member for shielding light, for example, may be disposed between the conversion element of the correction pixel 108 and the scintillator. In any conversion type of radiation imaging apparatus, a shield member may be disposed in a region in which the shield member overlaps on at least a portion of the conversion element of the correction pixel 108 in a plan view relative to the imaging region. As a result, sensitivity for conversion of a radial ray into an electric signal of the correction pixel 108 is lower than that of the detection pixel 101. By this, even in a case where not only the parasitic capacitances between the pixels 110 and the detection pixel 101 but also an operation temperature are changed and the characteristics of the individual elements are changed, information on irradiation with a radial ray may be more accurately generated by subtraction between the electric signals obtained from the detection signal line 104 and the correction signal line 103.

For example, in the case of the indirect irradiation imaging apparatus using a scintillator, the correction pixel 108 has a size, a structure of the conversion element, and a structure of the TFT which are the same as those of the detection pixel 101, and has a shield member formed of aluminum or chrome which shields light on a side on which a radial ray is incident relative to the conversion element. The shield member may be disposed between the scintillator and the conversion element, for example. Furthermore, the entire correction pixel 108 may be covered by a shield film so that detected light is substantially zero and a dark current of the conversion element and an offset level of the TFT portion are obtained so that correction of the detection pixel 101 may be performed using the obtained values.

The detection pixel 101 and the correction pixel 108 may be disposed adjacent to each other. Alternatively, the pixels 102 may be arranged in several columns, such as two columns as illustrated in FIG. 1, between the detection pixel 101 and the correction pixel 108. This is because, in the case where the detection pixel 101 and the correction pixel 108 are arranged adjacent to each other, a distance between the pixels 102 which sandwich the detection pixel 101 and the correction pixel 108 is increased. By inserting the pixels 102 between the detection pixel 101 and the correction pixel 108, an image of a portion of the detection pixel 101 and the correction pixel 108 in which a pixel lacks may be easily corrected. Sizes of sides of a pixel used in the radiation imaging apparatus 100 is as small as approximately 50 μm to approximately 500 μm, for example. Even in a case where two pixels 102 are disposed between the detection pixel 101 and the correction pixel 108, a relative distance between the detection pixel 101 and the correction pixel 108 is as short as approximately 150 μm to approximately 1.5 mm, and a temperature environment of the detection pixel 101 is seen to be the same as that of the correction pixel 108. Even in the case where the pixels 102 are arranged in several columns between the detection pixel 101 and the correction pixel 108, information on irradiation with a radial ray may be accurately generated and obtained. However, if parasitic capacitances of the plurality of pixels 102 associated with the detection signal line 104 are different from parasitic capacitances of the plurality of pixels 102 associated with the correction signal line 103, a difference is generated between crosstalk which overlaps with a signal of the detection signal line 104 and crosstalk which overlaps with a signal of the correction signal line 103. This is because, since the correction pixel 108 is connected to the correction signal line 103, the number of pixels 102 associated with the correction signal line 103 may be different from the number of pixels 102 associated with the detection signal line 104. Reduction of influence of this difference is required for improvement of correction accuracy. Furthermore, although in-plane distribution of intensity of an irradiated radial ray varies for each imaging, generated crosstalk may also vary depending on the number of correction pixels 108 in a region in which intensity of the irradiated radial lay is high. For example, in a case where the light-shielded correction pixel 108 associated with the correction signal line 103 is included in a region in which intensity of an irradiated radial ray is high, the number of pixels having electrodes in which potential change occurs associated with the correction signal line 103 is different from that of the detection signal line 104. Consequently, crosstalk generated in the correction signal line 103 and crosstalk generated in the detection signal line 104 are different from each other. Therefore, reduction of influence of a difference of the crosstalk generated for each imaging is required for improvement of correction accuracy.

Figure 2:
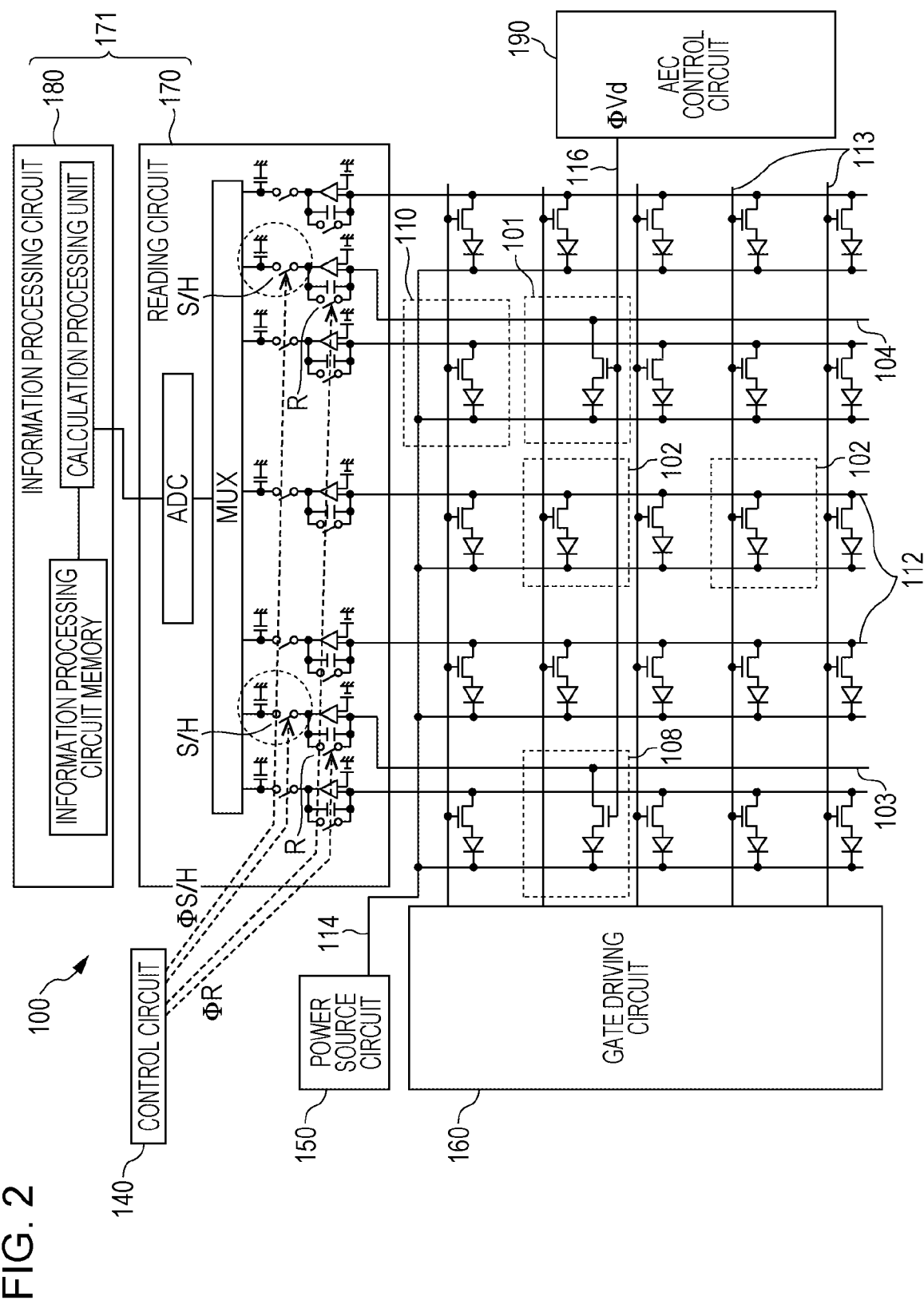
FIG. 2 is a diagram illustrating an equivalent circuit of a modification of the circuit configuration of the radiation imaging apparatus of FIG. 1.

FIG. 2 is a diagram illustrating an equivalent circuit indicating a circuit configuration of the radiation imaging apparatus 100 according to this embodiment and is a modification of the circuit configuration illustrated in FIG. 1. The equivalent circuit of FIG. 2 is different from the equivalent circuit of FIG. 1 in that the detection control line 116 which controls the detection pixel 101 and the correction pixel 108 is controlled by supplying the driving signal ΦVd using an AEC control circuit 190 which is disposed separately from the driving circuit 160 which controls the pixels 102 and 110. Other portions may be the same as those of the circuit configuration of the equivalent circuit of FIG. 1. Accordingly, the driving circuit 160 does not require a complicated operation when compared with the driving circuit 160 of the radiation imaging apparatus 100 illustrated in FIG. 1, and the driving circuit 160 is easily designed. For example, the AEC control circuit 190 is driven in a period of time from when a radial ray is emitted to when information on irradiation with a radial ray is read by the detection pixel 101 and the correction pixel 108. Thereafter, when the reading circuit 170 reads signals for obtaining a radiation image from the pixels 102 and 110, the AEC control circuit 190 may be stopped and the driving circuit 160 may be driven so that signals are successively read for each row. Furthermore, a device which operates the circuits in the peripheral region differently relative to the detection pixel 101 and the correction pixel 108 and the pixels 102 and 110 is not limited to the AEC control circuit 190. For example, in the reading circuit 170 of the signal processing circuit 171, signals from the detection signal line 104 and the correction signal line 103 may be processed separately from the pixels 102 and 110 by different reading circuits.

Figure 3A:
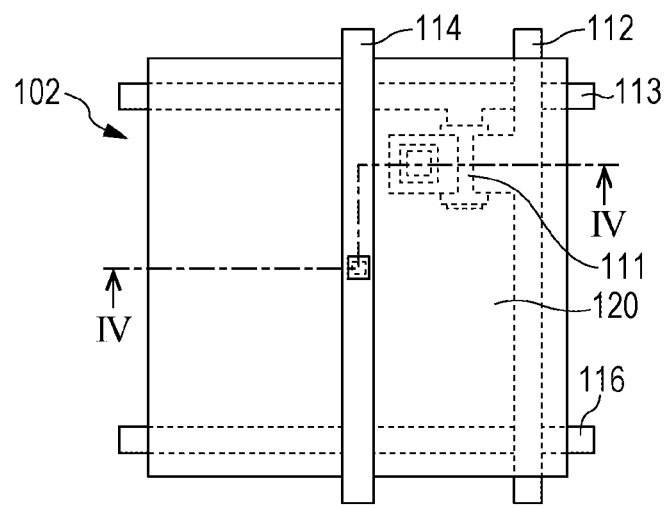
FIG. 3A is a plan view of a pixel of the radiation imaging apparatus of FIG. 1.

FIGS. 3A to 3D are plan views of the pixels 102 and 110, the detection pixel 101, and the correction pixel 108, respectively. FIG. 3A is a plan view of the pixels 102. In this embodiment, the radiation imaging apparatus 100 is an indirect radiation imaging apparatus and includes a scintillator (not illustrated) in an upper portion of the imaging region including the pixels 102 and 110, the detection pixel 101, and the correction pixel 108 arranged therein. Each of the pixels 102 includes a photoelectric conversion element 120 serving as the conversion element which converts light converted from a radial ray by the scintillator into an electric signal. In a lower portion of the photoelectric conversion element 120, a TFT 111 serving as the switch element and various lines are disposed. An electric signal generated by the photoelectric conversion element 120 through photoelectric conversion is output to the image signal line 112 through the TFT 111 when the TFT 111 is turned on in response to a signal supplied from the image control line 113. An upper electrode of the photoelectric conversion element 120 is connected to the power source line 114 which applies a constant voltage. The detection control line 116 passes the lower portion of the photoelectric conversion element 120. Although a number of the pixels 102 do not include the detection control line 116 passing therethrough as illustrated in FIGS. 1 and 2, the detection control line 116 passes through the pixel 102 in FIG. 3A.

Figure 3B:
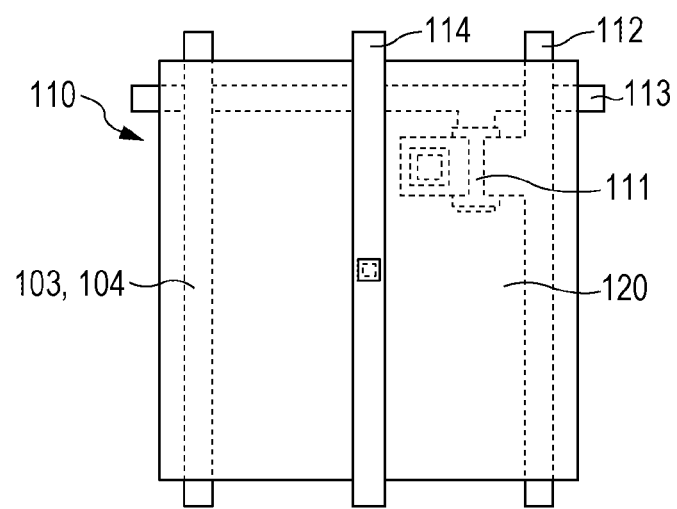
FIG. 3B is a plan view of a pixel of the radiation imaging apparatus of FIG. 1.

FIG. 3B is a diagram illustrating one of the pixels 110 including the detection signal line 104 or the correction signal line 103 passing therethrough in the pixel. The pixel 110 of FIG. 3B is the same as the pixel 102 except that the detection signal line 104 or the correction signal line 103 passes through the pixel 110. Different lower electrodes are disposed in the photoelectric conversion elements 120 of the different pixels 102 and the different pixels 110. Therefore, in the plan view relative to the imaging region, a capacitance corresponding to an overlap area is formed in a region in which the detection signal line 104 or the correction signal line 103 which passes through the pixel 110 overlaps with the lower electrode of the photoelectric conversion element 120. Charge accumulated in the photoelectric conversion element 120 is transferred to the detection signal line 104 or the correction signal line 103 through the capacitance based on the principle of conservation of charge.

Figure 3C:
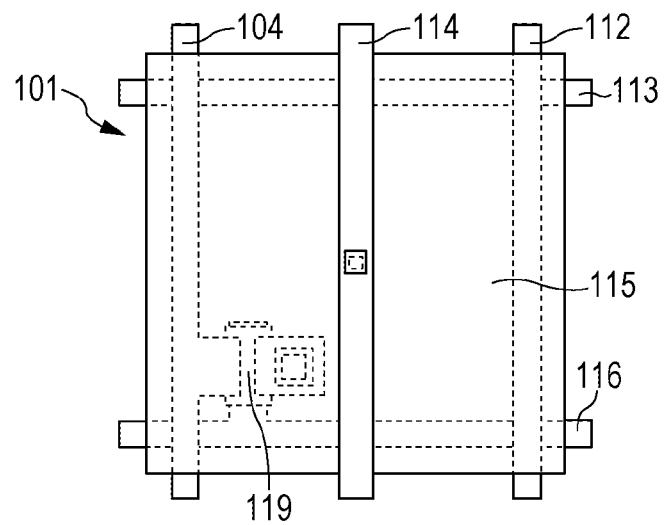
FIG. 3C is a plan view of a detection pixel of the radiation imaging apparatus of FIG. 1.

FIG. 3C is a diagram illustrating the detection pixel 101. The detection pixel 101 includes a photoelectric conversion element 115 included in a first conversion element which converts a radial ray into an electric signal and a TFT 119 serving as a first switch element which outputs the electric signal supplied from the first conversion element to the detection signal line 104. A lower electrode of the photoelectric conversion element 115 is connected to the detection signal line 104 through the TFT 119, and when the TFT 119 is turned on (brought into a conductive state) in response to a signal supplied from the detection control line 116, an electric signal supplied from the photoelectric conversion element 115 is output to the detection signal line 104. The TFT 119 is turned On and Off so that information on irradiation with a radial ray including measurement of illuminance obtained when a radial ray is emitted and detection of start and end of irradiation with a radial ray is obtained, and the reading circuit 170 reads signals accumulated in the photoelectric conversion element 115.

Figure 3D:
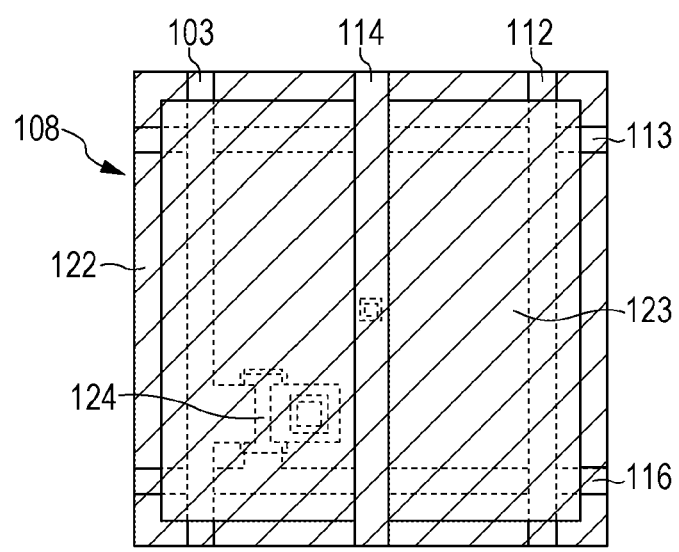
FIG. 3D is a plan view of a correction pixel of the radiation imaging apparatus of FIG. 1.

FIG. 3D is a diagram illustrating the correction pixel 108. The correction pixel 108 includes a photoelectric conversion element 123 included in a second conversion element which converts a radial ray into an electric signal and a TFT 124 serving as a second switch element which outputs the electric signal supplied from the second conversion element to the correction signal line 103. The correction pixel 108 includes a shield member 122 in a position between the scintillator (not illustrated) disposed in the upper portion of the imaging region and a photoelectric conversion element 123. In this embodiment, the correction pixel 108 and the photoelectric conversion element 123 disposed in the correction pixel 108 are entirely covered by the shield member 122. Since the shield member 122 is disposed, a difference is generated between an output value of an electric signal relative to a radial ray which is incident on the photoelectric conversion element 115 of the detection pixel 101 and an output value of an electric signal relative to a radial ray which is incident on the photoelectric conversion element 123 of the correction pixel 108. Specifically, the correction pixel 108 has sensitivity relative to a radial ray which is lower than that of the detection pixel 101, and sensitivity relative to an incident radial ray of the correction pixel 108 is lower than that of the detection pixel 101. Other configurations may be the same as those of the detection pixel 101 illustrated in FIG. 3C. A lower electrode of the photoelectric conversion element 123 is connected to the correction signal line 103 through the TFT 124, and when the TFT 124 is turned on (brought into a conductive state) in response to a signal supplied from the detection control line 116, an electric signal supplied from the photoelectric conversion element 123 is output to the correction signal line 103.

As described above, charge generated in the photoelectric conversion element 120 is output to the detection signal line 104 in accordance with the capacitance formed in the position between the detection signal line 104 and the photoelectric conversion element 120 of the pixels 110. Such pixels 110 are included in the imaging region, and the number of signals written by capacitance coupling between the photoelectric conversion elements 120 of the pixels 110 and the detection signal line 104 is not negligible. If several hundred or several thousand of such pixels 110 are included, the number of signals generated by the capacitance coupling may be several times to several tens of times as much as the number of electric signals of the detection pixel 101. Furthermore, even in a case where the photoelectric conversion element 120 does not overlap with the detection signal line 104, for example, charge is transferred from the photoelectric conversion element 120 due to spread of an electric field. Accordingly, by disposing the correction signal line 103 in a near region and obtaining a difference between the signals, the number of such signals transferred from the photoelectric conversion element 120 may be reduced and a signal supplied from the detection pixel 101 may be read by the reading circuit 170.

FIG. 4 is a cross-sectional view of one of the pixels 102 taken along a line IV to IV of FIG. 3A. The pixels and the elements are formed on a substrate 400 of the imaging region. In this embodiment, an insulation substrate is used as the substrate 400. A class substrate or a plastic substrate, for example, may be used as the substrate 400. The TFT 111 serving as a switch element is formed on the substrate 400. Although an inversely-staggered TFT is used in this embodiment, a top-gate TFT may be used, for example. The TFT 111 includes a gate electrode 401, source electrode 402, a drain electrode 403, and an insulation film 404. The insulation film 404 functions as a gate insulation film in the TFT 111. The photoelectric conversion element 120 is disposed on the TFT 111 through a protection film 405 and an interlayer insulation film 406. The photoelectric conversion element 120 is configured such that a first impurity semiconductor layer 412, an intrinsic semiconductor layer 413, and a second impurity semiconductor layer 414 of a conductive type opposite to the first impurity semiconductor layer 412 are laminated in this order between a lower electrode 411 and an upper electrode 415. The impurity semiconductor layer 412, the intrinsic semiconductor layer 413, and the impurity semiconductor layer 414 form a PIN photodiode which performs photoelectric conversion. Although the PIN photodiode is used as the photoelectric conversion element in this embodiment, an MIS element may be used, for example. Furthermore, the power source line 114 is disposed on the photoelectric conversion element 120 through a protection film 407 and an interlayer insulation film 408. The pixel 102 is covered by a protection film 409. The power source line 114 is connected to the upper electrode 415 of the photoelectric conversion element 120 through a contact plug. The lower electrode 411 of the photoelectric conversion element 120 is connected to the drain electrode 403 of the TFT 111. Charge generated by the photoelectric conversion element 120 due to the photoelectric conversion is output from the source electrode 402 to the image signal lines 112 when the TFT 111 is turned on by the gate electrode 401 connected to the image control lines 113.

Figure 5:
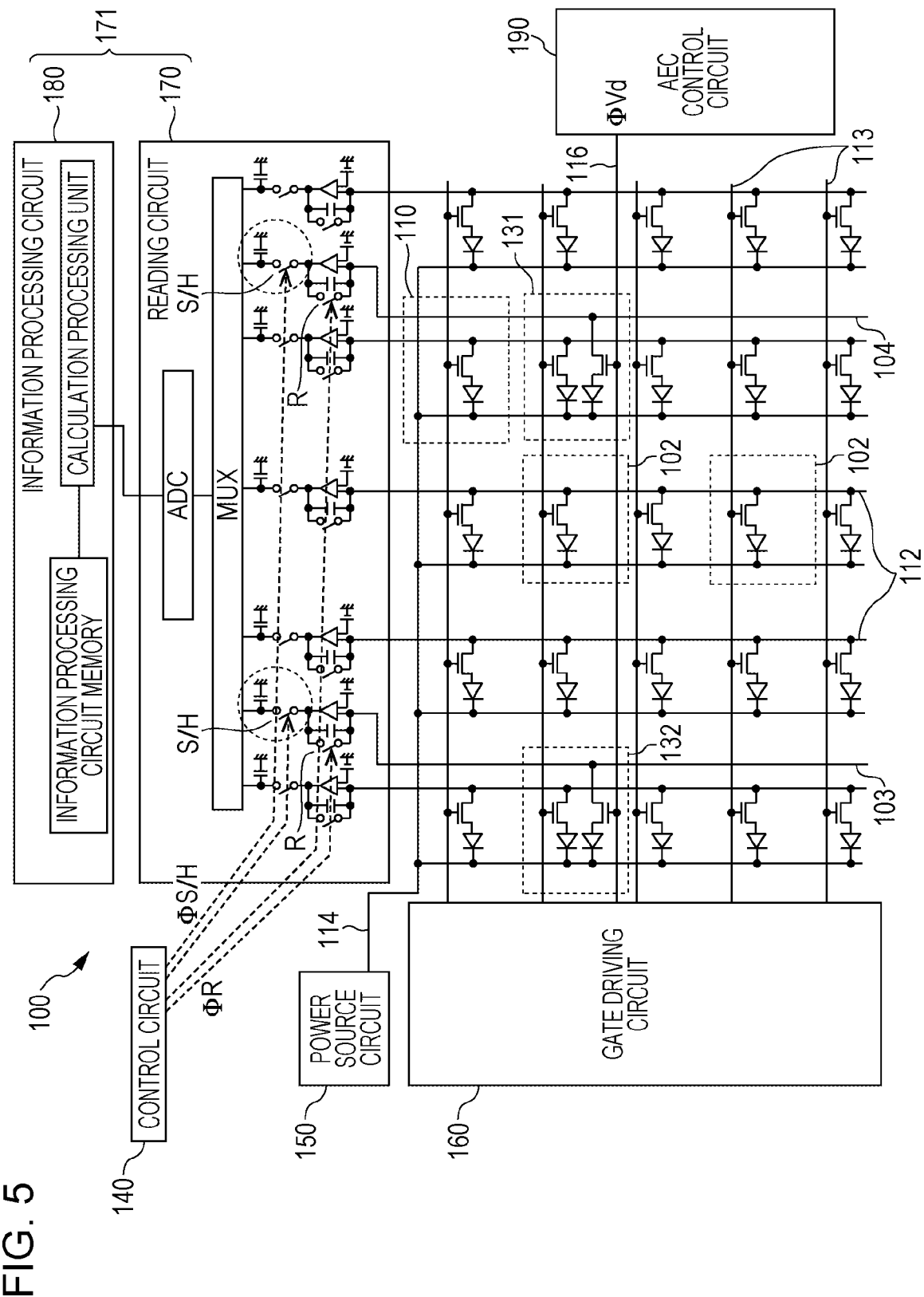
FIG. 5 is a diagram illustrating an equivalent circuit a modification of the circuit configuration of the radiation imaging apparatus of FIG. 1.

FIG. 5 is a diagram illustrating an equivalent circuit indicating a circuit configuration of the radiation imaging apparatus 100 according to this embodiment and is a modification of the circuit configuration illustrated in FIGS. 1 and 2. The equivalent circuit of FIG. 5 is different from those of FIGS. 1 and 2 in that, instead of the detection pixel 101 and the correction pixel 108, a pair of a detection pixel and an image pixel and a pair of a correction pixel and an image pixel are disposed as pixels 131 and 132. Other portions may be the same as those of the radiation imaging apparatus 100 illustrated in FIGS. 1 and 2. A conversion element for an image is disposed also in a region including a conversion element for detecting a radial ray so that lack of a pixel may be suppressed and correction of an image may be facilitated.

Figure 6A:
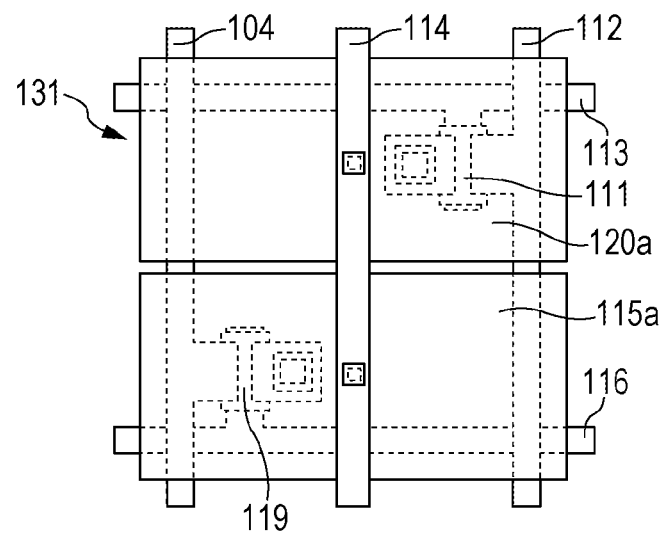
FIG. 6A is a plan view of a pixel of the radiation imaging apparatus of FIG. 5.
Figure 6B:
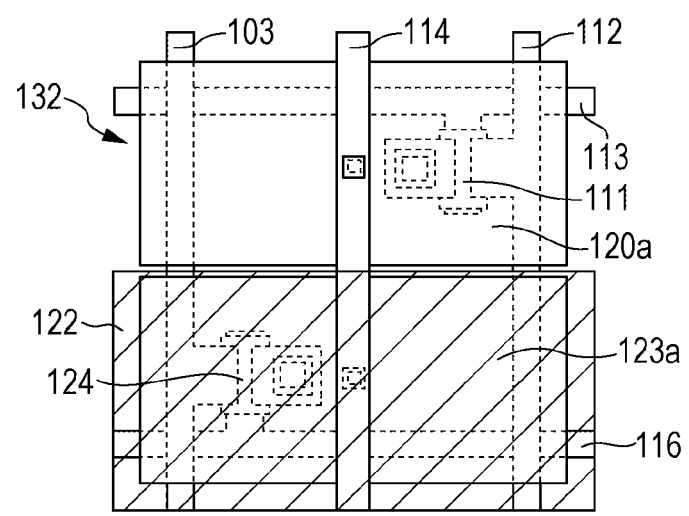
FIG. 6B is a plan view of a pixel of the radiation imaging apparatus of FIG. 5.

FIGS. 6A and 6B are plan views of the pixels 131 and 132 illustrated in FIG. 5, respectively. FIG. 6A is a plan view of the pixel 131. The pixel 131 has a configuration similar to the pixel 110 on an upper portion thereof, and includes a photoelectric conversion element 120a having an area smaller than that of the photoelectric conversion element 120 of the pixel 110. The pixel 131 has a configuration similar to the detection pixel 101 on a lower portion thereof, and includes a photoelectric conversion element 115a having an area smaller than that of the photoelectric conversion element 115 of the detection pixel 101. FIG. 6B is a plan view of the pixel 132. The pixel 132 has a configuration similar to the pixel 110 on an upper portion thereof, and includes a photoelectric conversion element 120a having an area smaller than that of the photoelectric conversion element 120 of the pixel 110. The pixel 132 has a configuration similar the correction pixel 108 on a lower portion thereof, and includes a photoelectric conversion element 123a having an area small than that of the photoelectric conversion element 123 of the correction pixel 108. Although the area of the photoelectric conversion element 120a is approximately a half of the photoelectric conversion element 120 of the pixels 102 and 110, an output equivalent to the pixels 102 and 110 may be obtained by image processing, such as offset correction and gain correction. The photoelectric conversion element 123a and the TFT 124 disposed in the pixel 132 may have the same configurations as the photoelectric conversion element 115a and the TFT 119 disposed in the pixel 131. Since the conversion elements and the TFTs in the pixels 131 and 132 have the same configurations, an offset level and a dark current which are output from the conversion elements and the TFTs and which are particularly changed in accordance with temperature may be corrected. Consequently, by subtracting a value of an electric signal obtained by the correction signal line 103 from a value of an electric signal obtained by the detection signal line 104, information on irradiation with a radial ray emitted to the detection pixel 101 may be accurately generated and obtained from the difference.

Figure 7:
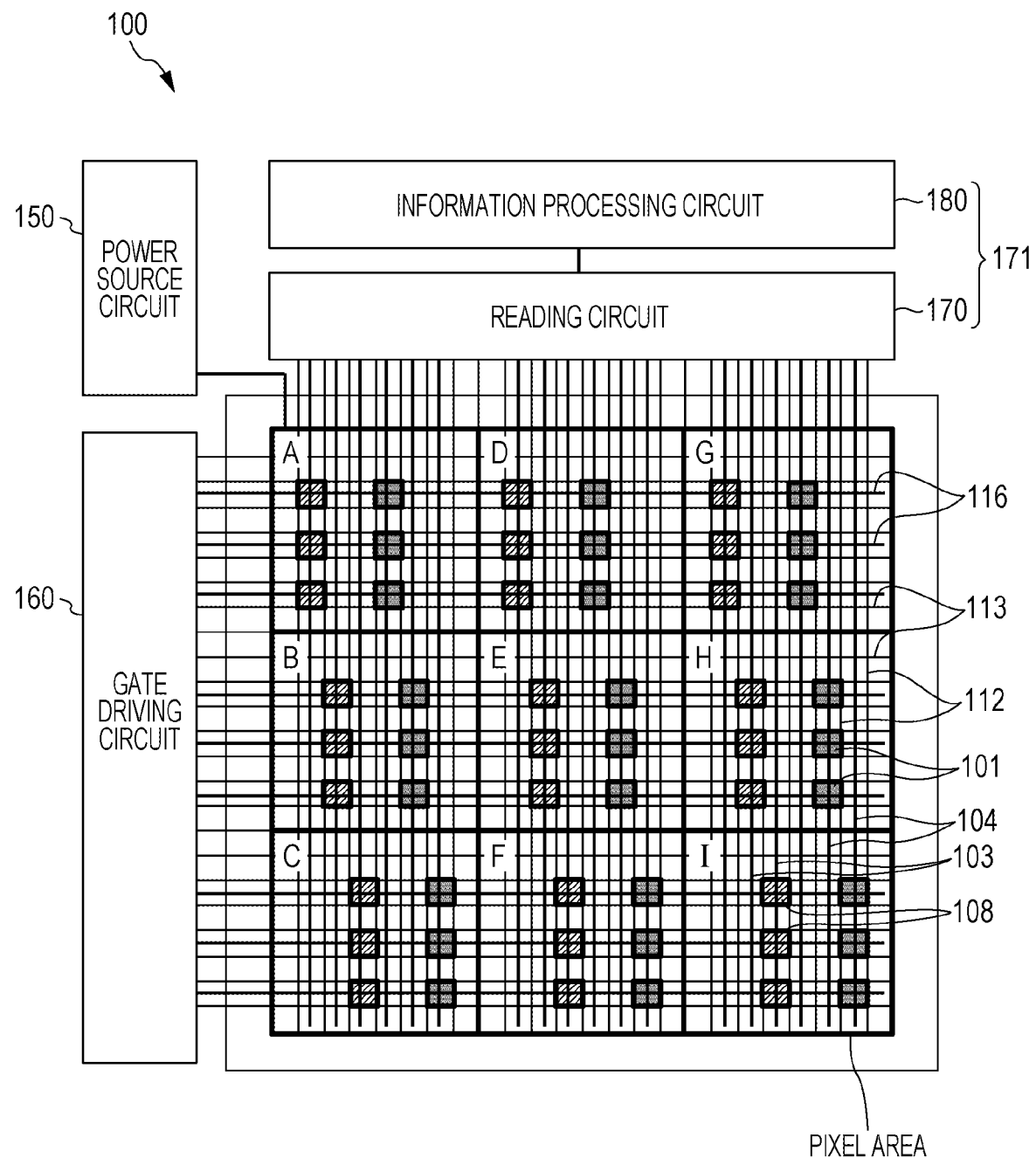
FIG. 7 is a diagram schematically illustrating layout in the radiation imaging apparatus of FIG. 1.

FIG. 7 is a diagram schematically illustrating layout in the radiation imaging apparatus 100 according to this embodiment. The equivalent circuits illustrated in FIGS. 1, 2, and 5 represent a partial region of the radiation imaging apparatus 100 as described above. FIG. 7 is the diagram schematically illustrating the layout in the entire radiation imaging apparatus 100, and a pixel area including the equivalent circuit illustrated in FIG. 1, for example, is disposed in nine regions, that is, in a matrix of 3 rows by 3 columns. Furthermore, the information on radiation emitted to the pixel areas may be collected by the reading circuit 170 and the information processing circuit 180 which are included in the signal processing circuit 171. Although the case where the single detection pixel 101 and the single correction pixel 108 are disposed in the single pixel area is illustrated in FIG. 1, three detection pixels 101 and three correction pixels 108 are disposed in a single pixel area in FIG. 7. The number of detection pixels 101 connected to the single detection signal line 104 may be the same as the number of correction pixels 108 connected to the single correction signal line 103. Furthermore, a sum of the number of pixels 110, the number of detection pixels 101, and the number of correction pixels 108 through which the single detection signal line 104 passes may be the same as a sum of the number of the pixels 110, the number of detection pixels 101, and the number of correction pixels 108 through which the single correction signal line 103 passes. Since the number of connected detection pixels 101, the number of connected correction pixels 108, the number of passed pixels 110, the number of passed detection pixels 101, and the number of passed correction pixels 108 are the same, information on irradiation with a radial ray on the detection pixels 101 may be accurately obtained. For example, as illustrated in a pixel area E, the detection pixels 101 and the correction pixels 108 may be disposed in a center portion of the imaging region which is far from an outer edge portion of the imaging region. The arrangement of the detection pixels 101 and the correction pixels 108 may be appropriately determined depending on a size or arrangement of a subject to be imaged.

The three detection pixels 101 in each of the pixel areas are connected to the common detection signal line 104, and the three correction pixels 108 are connected to the common correction signal line 103. Furthermore, the detection signal lines 104 and the correction signal lines 103 are shifted in a column direction such that the detection signal lines 104 and the correction signal lines 103 are not shared by the different pixel areas. With this configuration, when the detection control lines 116 are driven and signals are transferred from the detection pixels 101 and the correction pixels 106 to the signal processing circuit 171, for example, all the detection control lines 116 may be simultaneously operated. By simultaneously operating the detection control lines 116, an interval for reading a signal for obtaining the information on irradiation with a radial ray by the reading circuit 170 may be reduced when compared with a case where the signal is read during scanning, and accordingly, a reading speed is improved. Furthermore, in a case where the improvement of the reading speed is not required, the detection signal line 104 and the correction signal line 103 are shared among the pixel areas arranged in a vertical direction of FIG. 7, for example, and the detection control lines 116 are individually driven. By this, the processing circuit of the reading circuit 170 may be simplified and the number of terminals connected to the reading circuit 170 may be reduced.

Figure 8:
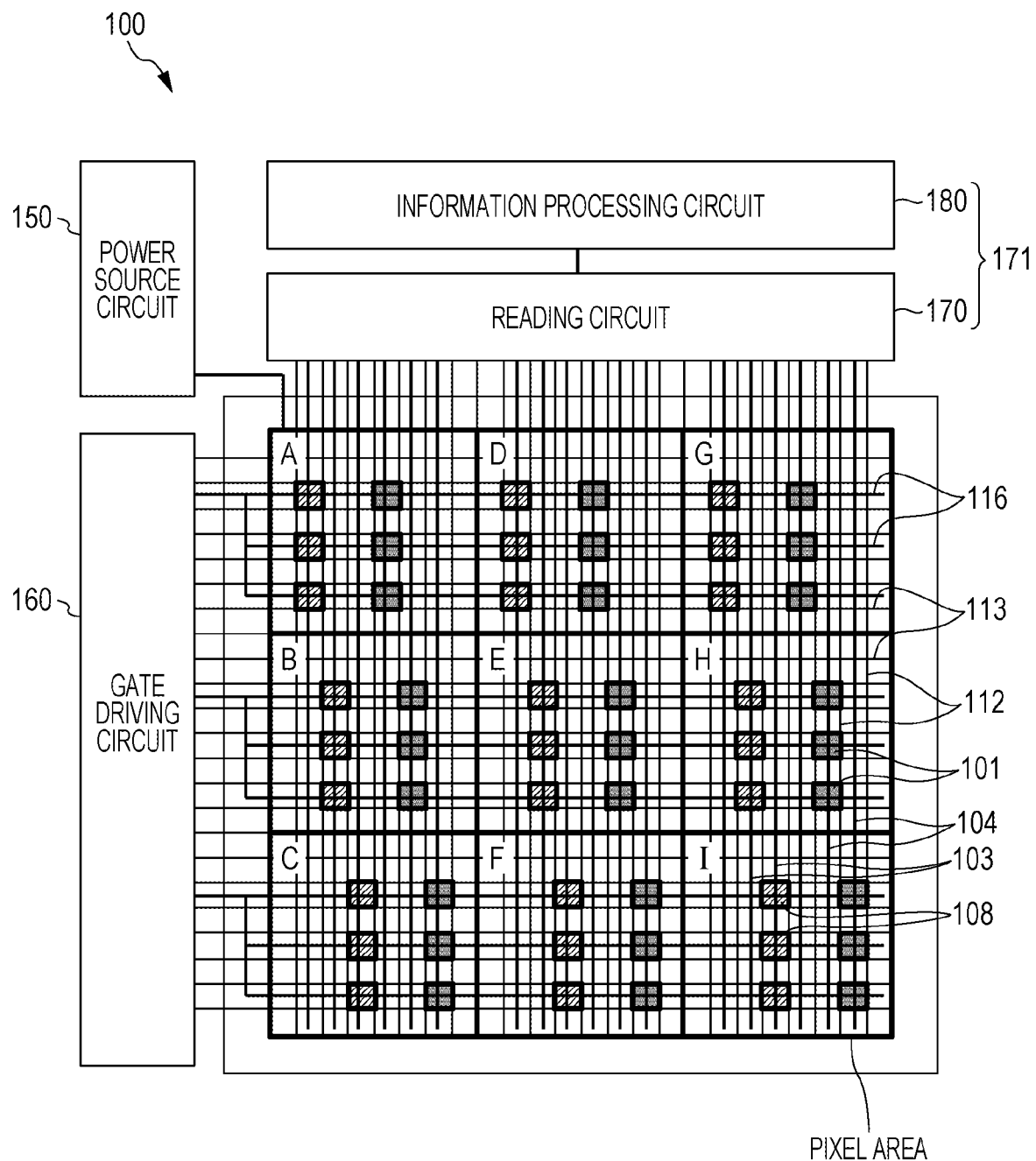
FIG. 8 is a modification of the diagram schematically illustrating the layout in the radiation imaging apparatus of FIG. 7.

FIG. 8 is a diagram schematically illustrating layout in the radiation imaging apparatus 100 according to this embodiment and is a modification of the layout diagram schematically illustrated in FIG. 7. The layout in FIG. 8 is different from that in FIG. 7 in that the detection control lines 116 are integrated before being connected to the driving circuit 160 for each pixel area. With this configuration, the driving circuit 160 may be simplified and the number of terminals connected to the driving circuit 160 may be reduced.

Figure 9:
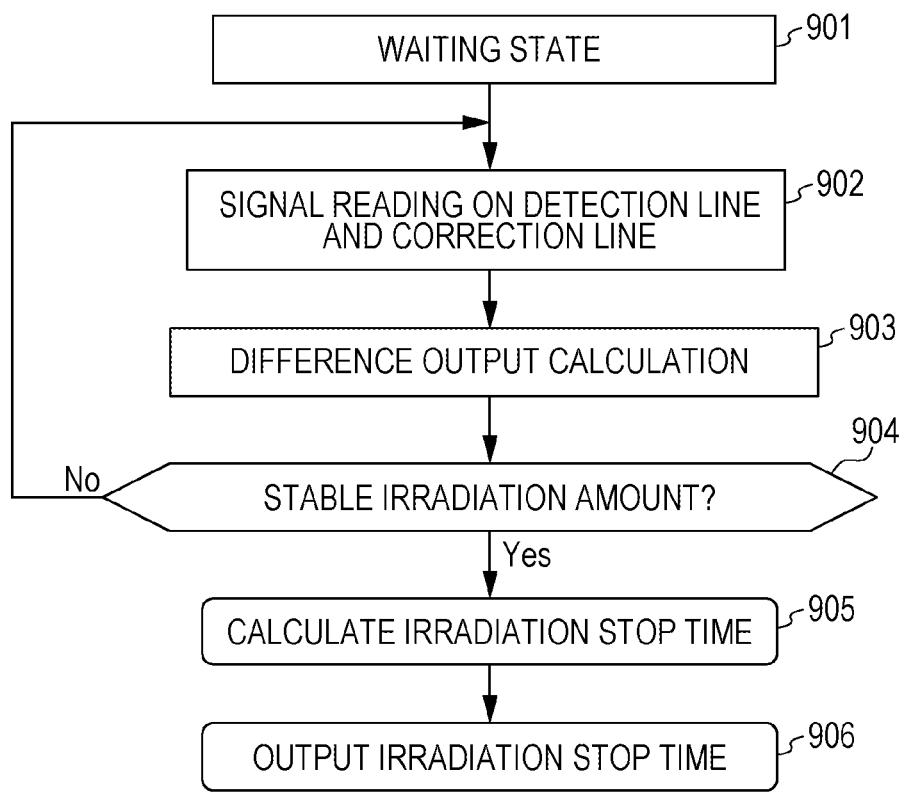
FIG. 9 is a flowchart of an operation of the radiation imaging apparatus of FIG. 1.

FIG. 9 is a flowchart of a process of detecting irradiation with a radial ray, determining irradiation intensity, and outputting an irradiation stop time which is performed by the radiation imaging apparatus 100 according to this embodiment. In step 901, the radiation imaging apparatus 100 maintains a waiting state. When irradiation with a radial ray is started, the process proceeds to step 902. Electric signals transferred through the detection signal line 104 and the correction signal line 103 are sampled in step 902, and a difference between the signals is extracted in step 903. The signal processing circuit 171 determines whether an irradiation amount of a radial ray is stable based on the difference in step 904. When the determination is negative, the process returns to step 902, and otherwise, the process proceeds to step 905. In step 905, the signal processing circuit 171 calculates a time point (an irradiation stop time) when the irradiation with a radial ray is to be stopped based on the difference. The calculated irradiation stop time is transmitted to a controller which controls a radiation source from the signal processing circuit 171 in step 906. The controller stops the irradiation with a radial ray based on the irradiation stop time. Although the radiation source is controlled by the signal processing circuit 171 of the radiation imaging apparatus 100 in this embodiment, the present invention is not limited to this. The calculation and the output of the irradiation stop time may not be performed but radiation information to be monitored may be output by the radiation imaging apparatus 100, and a determination of stop may be performed by a bulb and a control circuit which controls the bulb.

Figure 10:
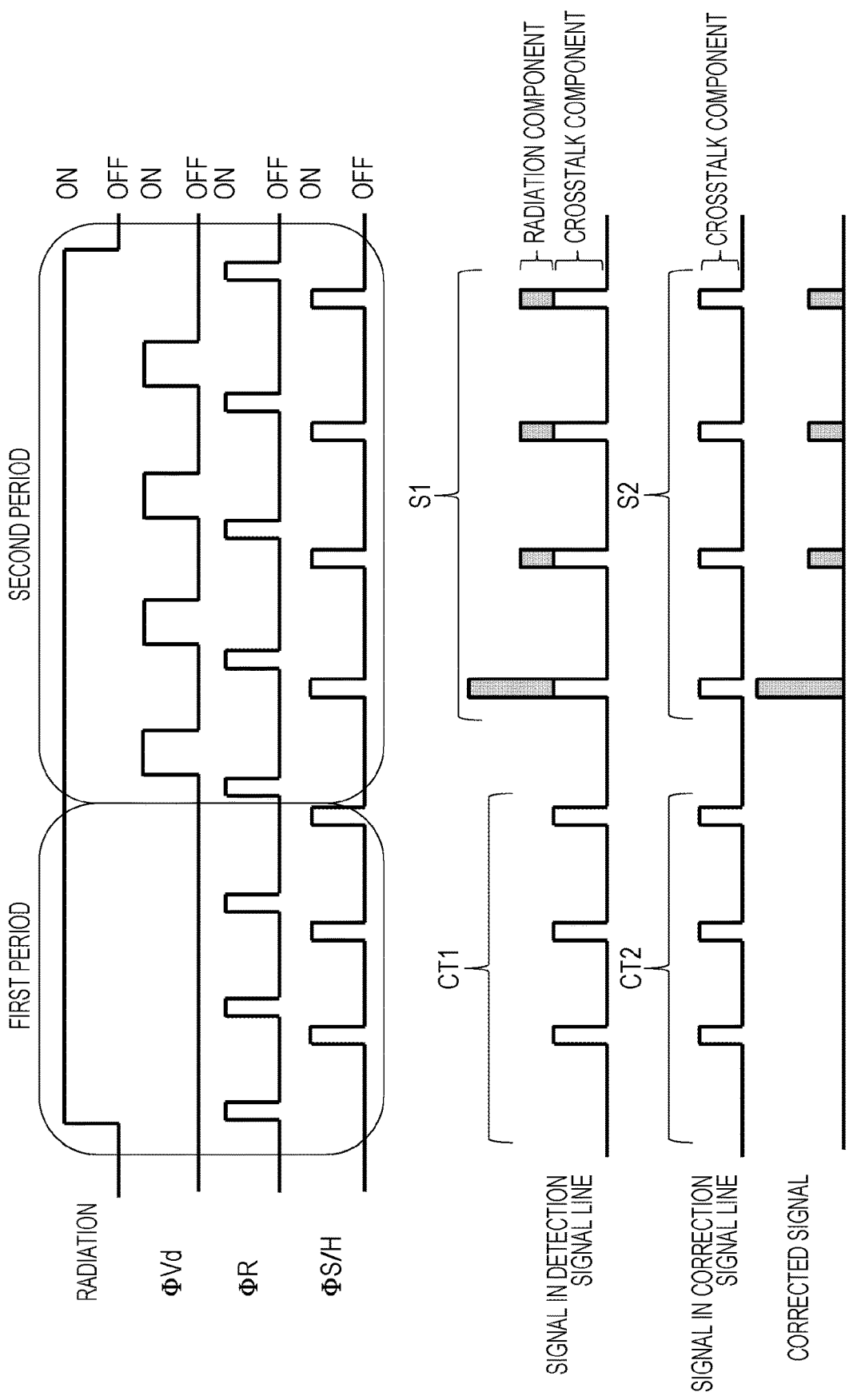
FIG. 10 is a timing chart of the operation of the radiation imaging apparatus according to the present invention.

Next, the operation of the radiation imaging apparatus 100 performed in step 902 to step 905 in FIG. 9 will be described with reference to FIG. 10. FIG. 10 is a timing chart of an operation controlled by the detection signal line 104 during irradiation with a radial ray is performed by the radiation imaging apparatus 100 according to this embodiment. Note that, in FIG. 10, the correction pixel 108 does not substantially have sensitivity to a radial ray.

First, when the control signal ΦR is brought into a high level, the reset switch R is turned on and the detection signal line 104 and the correction signal line 103 are reset. Immediately after the control signal ΦR is brought into a low level and the reset switch R is turned off, outputs of the detection signal line 104 and the correction signal line 103 start changing due to crosstalk. Subsequently, in a first period of an irradiation early period, a potential of a driving signal ΦVd of the detection control line 116 maintains in a low level, (the switch elements) of the detection pixel 101 and the correction pixel 108 are not turned on, the control signal ΦS/H are brought into a high level from a low level, and thereafter, the control signal ΦS/H is brought into a low level again. By this, the reading circuit 170 reads signals of crosstalk components which appear in the detection signal line 104 and the correction signal line 103 by the sampling performed by the sample-and-hold circuits S/H. A first operation which is a combination of the reset and the sampling is performed once or a plurality of times. Then the reading circuit 170 reads a signal CT1 (a first signal) of the crosstalk component of the detection signal line 104 and a signal CT2 second signal) of the crosstalk component of the correction signal line 103 once or a plurality of times.

Thereafter, in a second period after the first period during the irradiation with a radial ray, when the control signal ΦR is brought into a high level, the reset switch R is turned on and the detection signal line 104 and the correction signal line 103 are reset. Immediately after the control signal ΦR is brought into a low level and the reset switch R is turned off, outputs of the detection signal line 104 and the correction signal line 103 start changing due to crosstalk. Thereafter, a potential of the driving signal ΦVd of the detection control line 116 is brought into a high level from a low level, at least (the switch elements of) the detection pixel 101 and the correction pixel 108 are turned on, and thereafter, signals which appear in the detection signal line 104 and the correction signal line 103 are sampled. In the second period, a second operation which is a combination of the reset and the sampling is repeatedly performed. By this, the reading circuit 170 reads a signal S1 (a third signal) including a signal of a radiation component which is supplied from the detection pixel 101 and which appears in the detection signal line 104 and a signal of a crosstalk component once or a plurality of times. Furthermore, the reading circuit 170 reads a signal S2 (a fourth signal) including a signal of a radiation component which is supplied from the detection pixel 108 and which appears in the correction signal line 103 and a signal of a crosstalk component once or a plurality of times. Note that, since the correction pixel 108 does not substantially have sensitivity to a radial ray in the example of FIG.

10, the signal S2 does not substantially include a signal of a radiation component supplied from the correction pixel 108. Note that, in the second operation, the reset and the sampling may be performed while the switch elements in the pixels are in an On state. Furthermore, the switch elements of the pixels may be maintained in an On state during the second period.

The information processing circuit 180 performs a process of generating information on irradiation with a radial ray based on the signals CT1, CT2, S1, and S2. Here, the information processing circuit 180 performs a process of generating information on irradiation with a radial ray by correcting the signal S1 based on the signals CT1, CT2, and S2. The correction of the signal S1 may be performed by the information processing circuit 180 which calculates a rate of the signal CT1 to the signal CT2, corrects the signal S2 based on the rate, and performs a difference process on the signal S1 and the corrected signal S2. Specifically, the corrected signal S may be obtained in accordance with Expression (1) below.

$$S=S1-S2*(CT1/CT2) \qquad (1)$$

Furthermore, the correction of the signal S1 may be performed by the information processing circuit 180 which calculates a difference between the signal CT1 and the signal CT2, corrects the signal S2 based on the difference, and performs a difference process on the signal S1 and the corrected signal S2. Specifically, the corrected signal S may be obtained in accordance with Expression (2) below.

$$S=S1-(S2-(CT1-CT2)) \qquad (2)$$

Note that, the correction is performed in accordance with Expression (2) in a state in which an amount of irradiation with a radial ray per unit time is stable. Specifically, if an amount of irradiation with a radial ray per unit time in the first operation and an amount of irradiation with a radial ray per unit time in the second operation are substantially the same, the correction may be performed in accordance with Expression (2). In this way, when the correction is performed in accordance with Expression (2), a signal difference including a dark current and an offset level may be used as a correction value, and therefore, the dark current and the offset level may be subtracted in the second period.

In this way, correction accuracy may be improved in various imaging by obtaining the relationship between crosstalk components of the detection signal line 104 and the correction signal line 103 for each imaging. Note that the first period is performed in a period immediately after start of the irradiation with a radial ray to start of the second period so that generation of information on irradiation with a radial ray is immediately started. Note that, if correction is performed on an output obtained in a case where the first period is performed at any timing during the irradiation with a radial ray and a second period is set before the first period in accordance with a signal obtained in the first period, the effect of this embodiment may be obtained.

Figure 11:
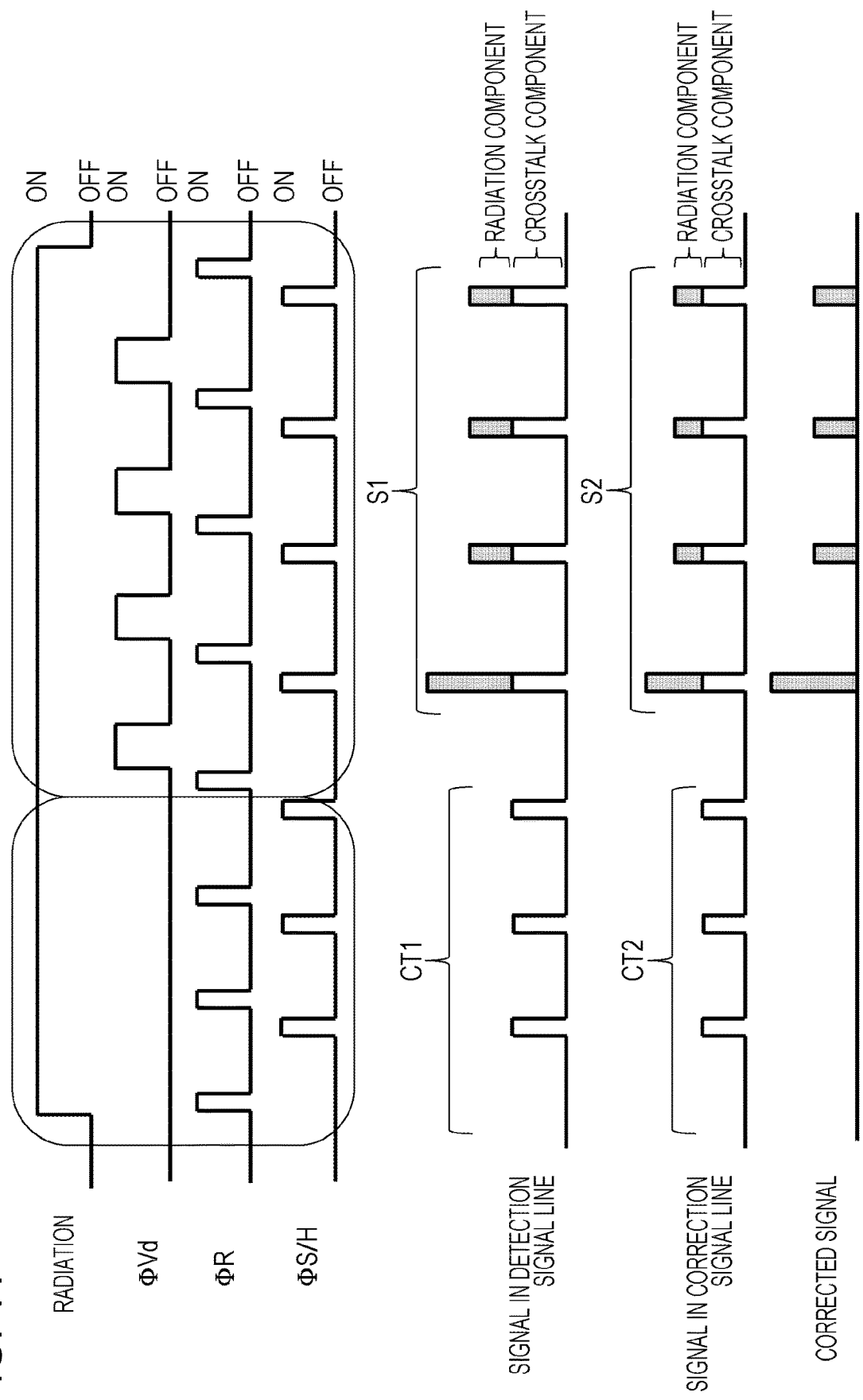
FIG. 11 is a timing chart of an operation of the radiation imaging apparatus according to the present invention.

Note that, although the correction pixel 108 does not substantially have sensitivity to a radial ray in FIG. 10, the present invention is not limited to this, and the correction pixel 108 may have sensitivity to a radial ray as illustrated in FIG. 11. Note that FIG. 11 is a diagram illustrating a case where the correction pixel 108 having sensitivity lower than that of the detection pixel 101.

Figure 12:
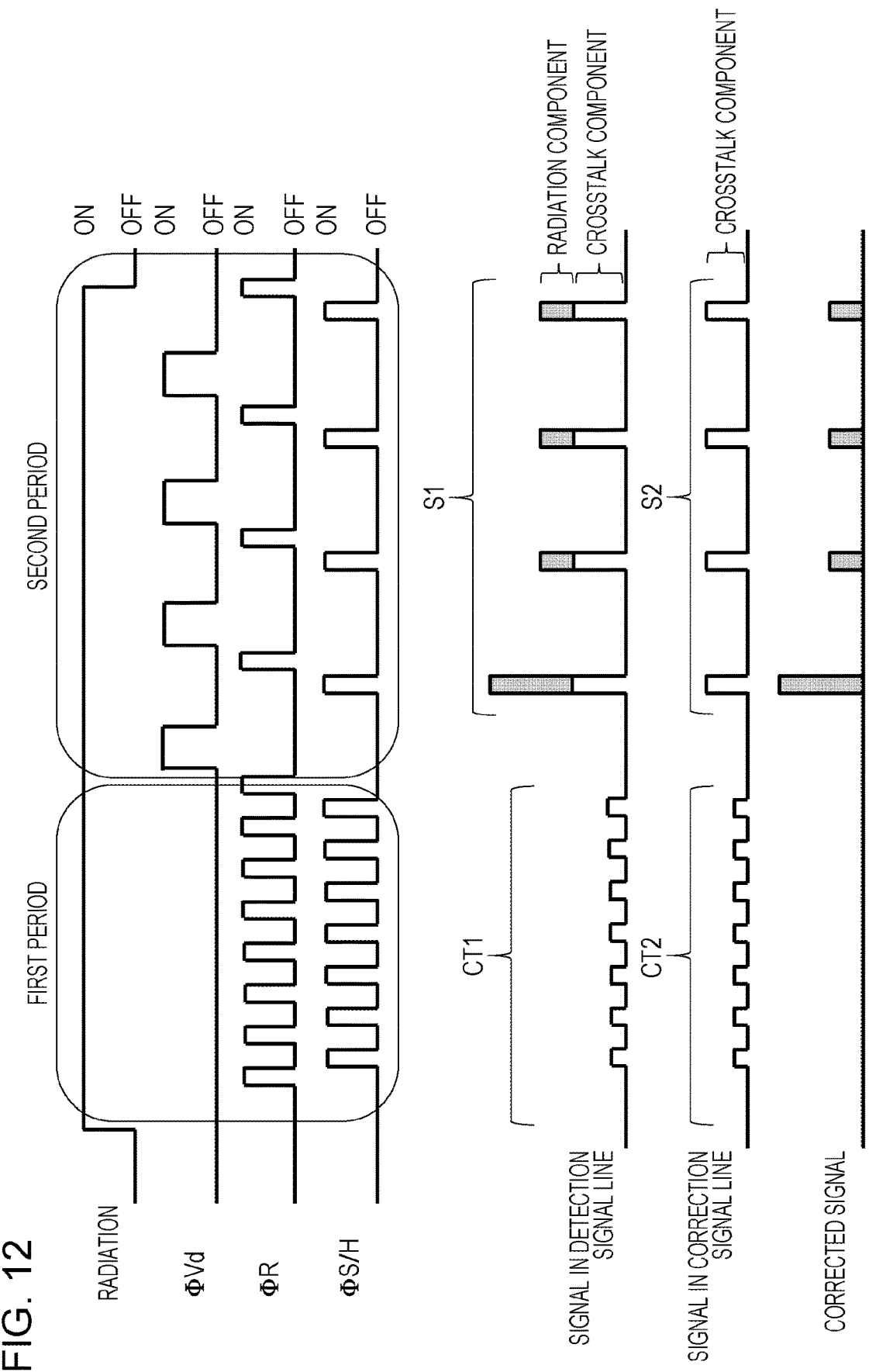
FIG. 12 is a timing chart of an operation of the radiation imaging apparatus according to the present invention.

Furthermore, although an operation cycle of the first operation performed a plurality of times is the same as an operation cycle of the second operation performed a plurality of times in FIG. 10, the present invention is not limited to this. As illustrated in FIG. 12, the operation cycle of the first operation performed a plurality of times may be shorter than the operation cycle of the second operation performed a plurality of times, that is, the first operation may be performed at higher speed than the second operation. In this case, the sampling may be performed a larger number of times per unit time when compared with the example of FIG. 10, and correction accuracy may be further improved. Furthermore, Expression (1) may be employed even in this case since amounts of crosstalk components per unit time are the same. Furthermore, even when Expression (2) is employed, correction may be performed if a difference between the signals CT1 and CT2 is multiplied by a rate of the operation cycles. Furthermore, different sampling intervals are employed in advance and a difference between the sampling intervals may be used as calibration data for correction.

Although the embodiments of the present invention has been described hereinabove, the foregoing embodiments may be appropriately changed or combined. Furthermore, design items which are easily assumed by those who skilled in the art are not described in detail, and the present invention is not limited to the embodiments. For example, the conversion elements, the scintillator, and the TFTs may be formed of different materials or different configurations, and the conversion elements may directly detect a radial ray. Furthermore, the entire photoelectric conversion elements 123 and 123a of the correction pixel 108 of FIG. 3D and the pixels 132 in FIG. 6B are shielded. However, any configuration may be employed as long as sensitivities to conversion between a radial ray and an electric signal have a difference between the detection pixel 101 and the correction pixel 108 or between the pixels 131 and 132, and an opening portion may be disposed on upper portions of the photoelectric conversion elements 123 and 123a so that partial light reaches the conversion element, for example. Furthermore, one of the detection signal line 104 and the correction signal line 103 which receive a signal output from the detection pixel 101 and the correction pixel 108, respectively, may be a common signal line which is also used as an image signal line which receives signals supplied from the conversion elements of the pixels 102.

Figure 13:
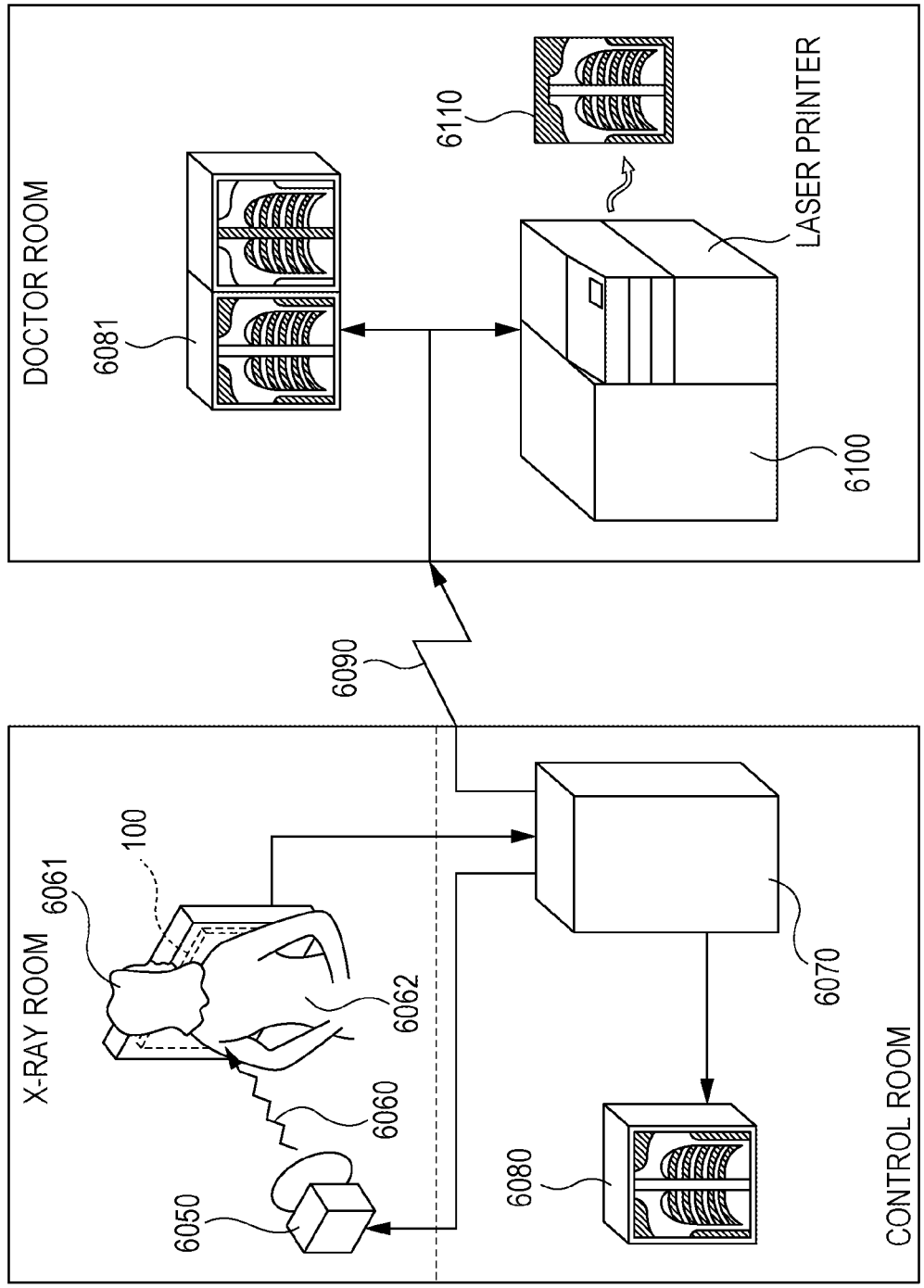
FIG. 13 is a diagram illustrating an example of a configuration of a radiation imaging system employing the radiation imaging apparatus.

Hereinafter, a radiation imaging system incorporating the radiation imaging apparatus 100 according to the present invention will be illustrated with reference to FIG. 13. An X ray 6060 generated in an X ray tube 6050 passes a breast 6062 of a patient or subject 6061 and is incident on the radiation imaging apparatus 100 according to the present invention. The incident X ray includes information on an internal-body portion of the patient or subject 6061. In the radiation imaging apparatus 100, the scintillator emits light in response to the incident X ray 6060, the light is subjected to photoelectric conversion by the photoelectric conversion elements so that electric information is obtained. This information is converted into digital information, subjected to image processing performed by an image processor 6070 serving as a signal processor, and observed through a display 6080 serving as a display unit in a control room. Furthermore, the information may be transferred to a remote location by a transmission processor, such as a telephone line 6090. By this, the information may be displayed in a display 6081 serving as a display unit installed in a doctor room in another location so that a doctor in the remote location may make a diagnosis. Furthermore, the information may be recorded in a recording medium, such as an optical disc or a film 6110 serving as a recording medium by a film processor 6100. Note that the X-ray tube 6050 may be controlled to stop irradiation with a radial ray based on the information on the irradiation with a radial ray generated by the information processing circuit included in the radiation imaging apparatus 100 according to the present invention.

Accordingly, a technique of improving accuracy of correction on a change of a signal caused by crosstalk and improving reliability of detection of a radial ray is provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus comprising:
a plurality of pixels which are arranged in an array in an imaging region and which are for obtaining a radiation image;
a first detection pixel including a first switch element and a second detection pixel including a second switch element and having sensitivity to detection of a radial ray which is different from sensitivity of the first detection pixel which are used to obtain information on irradiation with a radial ray on the imaging region including at least one of a start of irradiation with a radial ray, an end of irradiation with a radial ray, intensity of irradiation with a radial ray, and an amount of irradiation with a radial ray;
a first signal line which is disposed in the imaging region or adjacent to the imaging region and which receives a signal supplied from the first detection pixel through the first switch element in a conductive state;
a second signal line which receives a signal supplied from the second detection pixel through the second switch element in a conductive state;
a reading circuit configured to perform a first operation of reading first and second signals which appear in the first and second signal lines in a state in which the first and second switch elements are in a non-conductive state while the radiation imaging apparatus is irradiated with a radial ray and a second operation of reading third and fourth signals which appear in the first and second signal lines when the first and second switch elements are brought into a conductive state; and
an information processing circuit configured to perform a process of generating the information based on the first to fourth signals.

2. The radiation imaging apparatus according to claim 1, wherein the information processing circuit corrects the third signal based on the first, second, and fourth signals and generates the information.

3. The radiation imaging apparatus according to claim 2, wherein the information processing circuit calculates a rate of the first signal to the second signal, corrects the fourth signal based on the rate, corrects the third signal by performing a difference process on the third signal and the corrected fourth signal, and generates the information.

4. The radiation imaging apparatus according to claim 2, wherein the information processing circuit calculates a difference between the first and second signals, corrects the fourth signal based on the difference, corrects the third signal by performing a difference process on the third signal and the corrected fourth signal, and generates the information.

5. The radiation imaging apparatus according to claim 1, wherein the first and second detection pixels are disposed in the imaging region, and
wherein the second detection pixel has sensitivity to detection of a radial ray which is lower than sensitivity of the first detection pixel.

6. The radiation imaging apparatus according to claim 1, wherein each of the first and second detection pixels includes a conversion element which converts a radial ray into an electric signal, and
wherein the radiation imaging apparatus further includes a scintillator which converts a radial ray into light, the conversion element includes a photoelectric conversion element which converts light into an electric signal, and the second detection pixel includes a shield member which is disposed between the scintillator and the conversion element and which shields the light.

7. The radiation imaging apparatus according to claim 1, wherein the conversion element of the first detection pixel and the conversion element of the second detection pixel have the same structure.

8. The radiation imaging apparatus according to claim 1, wherein the first and second switch elements have the same structure.

9. The radiation imaging apparatus according to claim 1, wherein the number of first detection pixels connected to the first signal line and the number of second detection pixels connected to the second signal line are the same.

10. The radiation imaging apparatus according to claim 1, wherein the first signal line and the second signal line have respective regions which overlap with the plurality of pixels and the first and second detection pixels in a plan view relative to the imaging region, and
wherein a sum of the number of pixels which overlap with the first signal line, the number of first detection pixels, and the number of second detection pixels and a sum of the number of pixels which overlap with the second signal line, the number of first detection pixels, and the number of second detection pixels are the same.

11. The radiation imaging apparatus according to claim 1, further comprising:
a plurality of image signal lines which receive signals supplied from the plurality of pixels,
wherein one of the plurality of image signal lines also serves as the first signal line or the second signal line.

12. The radiation imaging apparatus according to claim 1, further comprising a plurality of image signal lines which receive signals supplied from the plurality of pixels.

13. The radiation imaging apparatus according to claim 1, wherein the information processing circuit performs control of a radiation source using the information on irradiation with a radial ray.

14. A radiation imaging system comprising:
the radiation imaging apparatus according to claim 1; and
a signal processing unit configured to process a signal supplied from the radiation imaging apparatus.

15. The radiation imaging system according to claim 14, further comprising:
a radiation source which generates a radial ray,
wherein the information processing circuit controls the radiation source based on the information.

* * * * *